(12) United States Patent
Gordilov

(10) Patent No.: US 11,576,401 B2
(45) Date of Patent: *Feb. 14, 2023

(54) PROTEIN SUSPENSION FROM BREWER'S GRAINS, METHOD AND APPARATUS FOR OBTAINING SAME

(71) Applicant: BioBo GmbH, Bad Berneck (DE)

(72) Inventor: Oleg Grigorievich Gordilov, Rostov-na-Donu (RU)

(73) Assignee: BioBo GmbH, Bad Berneck (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/049,013

(22) PCT Filed: Oct. 24, 2019

(86) PCT No.: PCT/RU2019/000766
§ 371 (c)(1),
(2) Date: Aug. 26, 2021

(87) PCT Pub. No.: WO2021/080450
PCT Pub. Date: Apr. 29, 2021

(65) Prior Publication Data
US 2021/0378260 A1     Dec. 9, 2021

(30) Foreign Application Priority Data

Oct. 21, 2019  (RU) .................................. 2019133308

(51) Int. Cl.
*A23J 1/12*     (2006.01)
*A23L 33/175*   (2016.01)
(Continued)

(52) U.S. Cl.
CPC ............... *A23J 1/12* (2013.01); *A23L 33/115* (2016.08); *A23L 33/175* (2016.08);
(Continued)

(58) Field of Classification Search
CPC ........ A23J 1/12; A23J 3/14; A23J 1/16; A23L 33/75; A23L 33/115; A23L 33/21;
(Continued)

(56) References Cited

U.S. PATENT DOCUMENTS

| 5,135,765 A | 8/1992 | Kishi et al. |
| 5,156,877 A | 10/1992 | Kishi et al. |
| 5,702,748 A | 12/1997 | Kishi et al. |

FOREIGN PATENT DOCUMENTS

| EA | 018932 B1 | 11/2013 |
| EP | 0694609 A2 | 1/1996 |

(Continued)

OTHER PUBLICATIONS

Ibbett et al. Innovative Food Science and Emerging Technologies 56 (2019) 102184, pp. 1-9. (Year: 2019).*

(Continued)

*Primary Examiner* — Subbalakshmi Prakash
(74) *Attorney, Agent, or Firm* — BCF LLP

(57) ABSTRACT

The group of inventions relates to the food industry, and more particularly to a method and device for transforming brewer's spent grain (BSG). The invention makes it possible to increase the level of recovery of edible fractions from BSG to 90-95%, and to increase the amount of protein in an edible suspension to not less than 50 wt % dry solids. The underlying principle of the invention is a technique for preparing BSG for nutrient extraction and extracting said nutrients by mechanical processing on a proposed industrial processing line. The essence of the claimed method lies in loosening BSG on a vibratory sieve, grinding the BSG in a colloid mill with the addition of water or centrate in a ratio of from 0.5:1 to 1:1 relative to BSG to produce a paste-like homogeneous mass of BSG, and then processing said mass in a screw extractor for further grinding and separation into two fractions: an edible suspension having a 90-95% mois- (Continued)

ture content and containing all of the nutrients of BSG, including protein substances; and ground BSG husks having a 60-75% moisture content, suitable for subsequent industrial use. The edible suspension is then mechanically filtered to remove ground husk residue, and the suspension is pumped into a storage tank.

8 Claims, 2 Drawing Sheets

(51) Int. Cl.
*A23L 33/115* (2016.01)
*A23L 33/21* (2016.01)
*A23L 33/185* (2016.01)
*B02C 4/04* (2006.01)
*C12P 21/06* (2006.01)
*C12P 21/02* (2006.01)

(52) U.S. Cl.
CPC .............. *A23L 33/185* (2016.08); *A23L 33/21* (2016.08); *B02C 4/04* (2013.01); *C12P 21/06* (2013.01); *C12P 21/02* (2013.01)

(58) Field of Classification Search
CPC ....... A23L 33/185; A23L 33/175; B02C 4/04; C12P 21/02; C12P 21/06; A23K 10/38; Y02P 60/87; A23V 2002/00; A23V 2250/5482
USPC ........................................................ 530/372
See application file for complete search history.

(56) References Cited

FOREIGN PATENT DOCUMENTS

| KZ | 16531 A | 8/2003 |
|---|---|---|
| RU | 2109059 C1 | 4/1998 |
| RU | 2215426 C2 | 11/2003 |
| RU | 2335918 C2 | 10/2008 |
| RU | 2577021 C1 | 3/2016 |
| RU | 2592568 C1 | 7/2016 |
| WO | 9822751 A1 | 5/1998 |
| WO | 2010053493 A1 | 5/2010 |
| WO | 2010117288 A1 | 10/2010 |
| WO | 2018136234 A1 | 7/2018 |

OTHER PUBLICATIONS

Rudenko "Modern trends in processing of major brewing by-products", Beer and Beverages, 2007, No. 2, 66-68 in Russian Language.
Machine translation into English of Rudenko "Modern trends in processing of major brewing by-products", Beer and Beverages, 2007, No. 2, 66-68.
Kolpakchi "Secondary material resources of brewing", Agropromizdat, 1986, 86-89 (in Russian).
Search report dated May 18, 2020 in respect of the corresponding eurasian patent application EA201900521.
Ahmetvaliev "Analysing the Process of Suspension Fractionating and Improving the Vibrational Centrifuge", APK Russia 2015, issue 74, pp. 9-14 (abstract only).
Machine translation from Russian into English of Abstract for Kolpakchi "Secondary material resources of brewing", Agropromizdat, 1986, 86-89.

* cited by examiner

A

B

C

PROTEIN SUSPENSION FROM BREWER'S GRAINS, METHOD AND APPARATUS FOR OBTAINING SAME

TECHNICAL FIELD

This group of inventions is referred to food-processing industry and is related to technologies of processing the brewing industry wastes, namely a method and a machine for processing brewer's grains in order to obtain a protein product in the form of suspension that can be used as food stuff with health-promoting and dietary properties. In particular, protein derived from brewer's grains is of the most significant interest for use in bakery, pastry, sausage manufacture, sport and dietary nutrition. Besides, the invention can be used as a feed supplement in livestock farming, as a soil fertilizer in agriculture etc.

BACKGROUND OF THE INVENTION

After producing beer brewing companies have a lot of wastes in the form of brewer's grains consisting of remains of barley glume and grain particles rich in protein and fat. This brewer's (malt spent) grains raise the greatest interest among all secondary raw material resources of the brewing industry because they are produced in great numbers and they contain a lot of valuable nutritional ingredients.

Brewer's grains are obtained at the stage of filtering saccharified brewer's mash. Percentage of brewer's grains in the brewing industry wastes amounts to at least 98%. Brewer's grains consist of liquid and solid phases. The solid phase that accounts for approximately 45% in brewer's grains is represented by glume and grain kernel particles. In brewer's grains, there are fats, fibres and amino acids: histidine, lysine, leucine, isoleucine, methionine, valine, glycine, threonine, serine, alanine, arginine, phenylalanine, tyrosine etc. Every year Russian brewing companies dispose of more than 3.5 min tons of brewer's grains where the protein content amounts to 25-28% what is almost by 3 times higher than the protein content in barley. Caloric density of wet grains amounts to 115 cal/g and of dry grains to 440 cal/g (with the humidity level of 7-10%). Ingredients in brewer's grains depend on the type of barley; technologies used for manufacturing brewer's malt; malt mix recipe for manufacturing beer; malt grout recipes for manufacturing beer etc. However, the obtained quantitative composition of proteins, fats, hydrocarbons and fibres in brewer's grains varies slightly from 1 to 5%.

At present, brewer's grains in their native form are not extensively used because their transportation and storage are complicated by the fact that fermentation processes are initiated in such brewer's grains in 6-8 hours at the temperature of 15-30° C. and the grains become unsuitable for processing and further use.

Prior art solutions comprise various methods of processing brewer's grains for their use as a feed supplement based on their preliminary frying with further granulation or grinding (for example, EP0694609A2; WO2010053493A1; WO2010117288A1; WO9822751A1). However, in the course of drying a part of protein substances is transformed into a non-digestible form what causes decrease in nutritional value of dry brewer's grains in comparison with wet brewer's grains. The final protein content in dried brewer's grains amounts to only 27-28%. Besides, this product contains significant amounts (up to 80%) of non-digestible barley malt husk. Besides, drying of brewer's grains requires great power consumption because of which it is not always economically reasonable to make feed stuff from such brewer's grains.

Prior art solutions also include methods of deeper processing of wastes from the brewing industry. In particular, there is a known method of processing liquid brewer's grains with the humidity level of 90-92% that envisages treatment of the source raw materials by means of two-step compression: down to the humidity level of 70-75% during the first step and down to the humidity level of 40-45% during the second step, and two-stage drying: down to the humidity level of 20-25% during the first stage and down to the humidity level of 10% during the second stage with obtaining of a dry feed supplement (RU2215426). This method has a shortcoming: centrate containing a significant amount of nutrients is removed in the course of compression. Besides, the final product is also characterized with high content of barley husk.

Another prior art solution comprises a method of deriving a protein product from brewer's grains with the protein content from 60% to 90% (WO2018136234A1). This method implies thermochemical treatment of brewer's grains when the following is done: a mixture consisting of worked-out grains and water is added in a hydrolysis tank with constant stirring; then glucoamylase is added; the obtained mixture is heated up to the temperature from 30 up to 70° C.; grain particles in the said mixture are subject to grinding in order to obtain the medium size of max. 500 micrometer; then the mixture pH is brought to the level approximately from 7 to 10.5 and then alkaline protease is added for the purpose of protein solubisation. The obtained mixture is screened with the screen plate's diameter from 5 to 500 micrometer; then ultrafiltration with the use of membranes with their pore size from 20 kDa to 40 kDa is performed and then nanofiltration is performed. This method's shortcoming is a necessity of using sophisticated and expensive equipment, long technological cycle for obtaining the protein product (60-105 minutes, including 30-60 minutes for the grinding process and 30-45 minutes for hydrolysis) and the use of hazardous substances—hydrochloric or carboxylic acids and alkalis—in this technological process. Besides, in the course of processing brewer's grains great amounts of water from 8:1 to 11:1 in relation to brewer's grains are used as a result of which a lot of centrate is formed. Such centrate is a waste product and additional equipment is required for its disposal.

Another prior art solution (method known as EP0694609A2) implies obtaining a protein composition from grain material worked-out in the course of making beer. This composition contains from 40 to 60% of proteins, from 12 to 18% of lipids, from 2 to 6% of fibre materials and from 1 to 4% of ash in terms of the equivalent amount of dry weight. This method implies compression of brewer's grains by means of a roller-grinding machine with simultaneous wet peeling of grain particles and further separation of the obtained product from the husk. The method has a shortcoming: a number of valuable components are removed from brewer's grains in the course of compression by means of roller grinding machines. Besides, brewer's grains are not subject to grinding before compression and a part of protein remains inside compressed husk particles due to which this protein is lost with the further husk removal. Besides, in order to enhance the husk removal efficiency in accordance with the known method the obtained mixture (liquid protein suspension) is rinsed with large quantities of water, then the obtained suspension is screened by means of screen plates. This rinsing and screening process is repeated up to 5 times.

As a result, a great amount of centrate is produced. Such centrate is a waste product and additional purification equipment is required for its disposal.

Thus, all existing methods of processing brewer's grains are aimed at obtaining protein powders or concentrates and they are characterized by complexity and duration of the protein production process, high output of centrate that is a waste product requiring additional equipment for its disposal.

Prior art solutions do not have any method of processing brewer's grains and obtaining the final product in the form of protein suspension rich in protein that can be widely used as a food and feed supplement. The known methods are mainly aimed at obtaining from brewer's grains a product in the form of powder or concentrate without deriving in the course of technological processes a ready-for-use product that extends the range of dietary food products.

DISCLOSURE OF THE INVENTION

The technical result of the claimed group of inventions is a product obtained in the course of processing brewer's grains in the form of suspension with the protein content of min. 50% wt (dry solid) with the nutritional energy value of 250 ±15 kcal with a simplified production method. The suspension is a ready-for-use product or an intermediate product from which concentrate, isolate or powder with the protein content of 90-95% wt (dry solid) can be derived in the course of further treatment. At the same time, the amount of centrate being a waste product and subject to disposal is minimal because of its use in the technological cycle for humidifying the source raw material subject to processing.

The technical result is achieved by means of protein suspension obtained from brewer's grains with the humidity level of 90-95% and with the particle size of max. 0.5 mm.

At the same time, the suspension composition is optimal as it contains proteins, fats, fibre, ash and amino acids in the following (dry solid) amount, % wt:
 proteins—min. 50.0
 fats—min. 5.0
 fibre—max. 5.0
 ash—max. 1.5
at the same time amino acids content amounts to min. 47.0.

The technical result is also achieved by means of a method for obtaining such protein suspension. It implies that the source brewer's grains are loosened up in order to obtain a homogeneous mass; foreign impurities are removed; the mass is humidified with its further grinding with simultaneous homogenization by means of a colloid mill in order to obtain a pasty mass (pulp); at the same time, humidifying up to the humidity level of max. 95% is performed by means of supplying water or centrate in the course of loading brewer's grains into the colloid mill; after that the ground husk is removed from the pulp and the final product in the form of food suspension with the protein content of min. 50% wt (dry solid) is obtained. At the same time, before producing a homogeneous mass, foreign impurities are removed by means of a vibrating screen with the hole size of 6-10 mm and the screen vibration frequency from 10 to 50 Hz and the amplitude of 2-20 mm. The raw materials are subject to grinding by means of a colloid mill with the rotor frequency of 1,800-3,200 rot./second in order to produce 0.10-0.9 mm particles. In the course of loading brewer's grains into the colloid mill water or centrate is supplied in order to provide for homogeneous humidifying of the raw materials in volume. After grinding in the colloid mill, the ground husk is removed by means of a screw extractor. Then the food suspension is subject to additional vibrating filtration with the use of screens with the hole size of 0.1-0.5 mm for the purpose of removing remaining husk particles.

Besides, the technical result is achieved due to the use of a machine for obtaining the claimed protein suspension comprising the following components connected in a particular sequence: a device for loosening and removing foreign impurities; a grinding machine designed with a possibility of humidifying raw materials in volume, grinding these materials in order to obtain the fraction of 0.1-0.9 mm and homogenization; an extractor designed with a possibility of additional grinding of the mass in order to produce 0.005-0.5 mm particles and its division into suspension and husk; a vibration filter with the hole size of 0.2-0.5 mm designed with a possibility of additional separation of remaining husk particles from the suspension; a container for collecting the protein suspension. At the same time, a vibrating screen with a magnetic catcher with the hole size of 6-10 mm and the screen vibration frequency from 10 to 50 Hz and the amplitude of 2-20 mm is used as a device for loosening and removing foreign impurities. A colloid mill equipped with a tool for water supply for the raw material humidifying is used as a grinding machine. This colloid mill consists of a V-shaped tank; for the purpose of uniform humidifying of the raw materials it contains a tool designed in the form of a water pipeline with openings and nozzles located around the circumference of the tank in its upper part above the mark indicating the maximum tank load with raw materials. A screw extractor with the screw rotation rate from 2 rot./minute to 8 rot./minute is used as an extractor. In addition, the machine has a block for concentrating the protein suspension equipped with an out channel for centrate connected with the grinding machine for humidifying the supplied raw materials.

The produced protein suspension is characterized with a high protein content that is achieved by means of grinding brewer's grains with addition of water or centrate in the colloid mill, thorough separation of brewer's grain husk from the food part in the screw separator with additional grinding of the processed mixture in the course of rubbing the mixture against the separator's filtering mesh by means of its screw. Besides, no centrate is accumulated in the course of processing brewer's grains in order to obtain the final product in the form of suspension. For the purpose of producing concentrate, isolate or powder during the suspension further treatment, the produced centrate is sent for recycle for humidifying the source raw materials and its quantity sent for disposal amounts to max. 1% from the manufacturing capacity of the brewer's grains processing line of kg/1 min.

Figure 3:
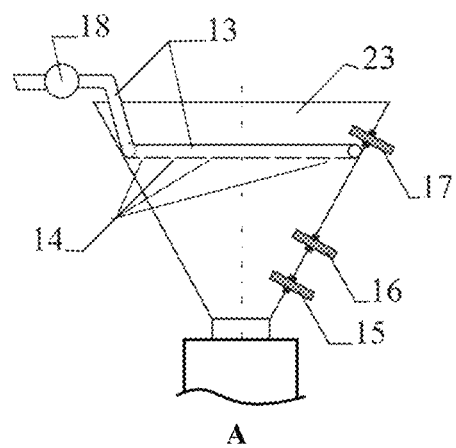
Figure 3:
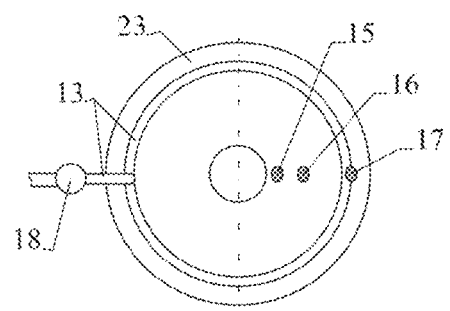
Figure 3:
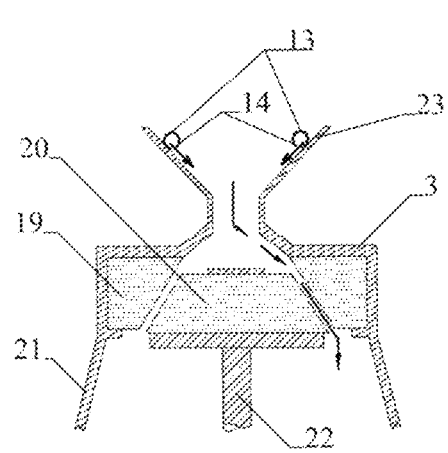

FIG. 3 demonstrates a scheme of the colloid mill's loading tank. A indicates a layout of constructive elements in the colloid mill's loading tank, B indicates an overhead view of the loading tank, C indicates a cross-section diagram of the colloid mill, where 13 indicates a circular water pipeline, 14 indicates openings in the pipeline for water or centrate supply, 15, 16 and 17 indicate level-sensing devices, 18 indicates a control valve for water supply, 19 indicates a stator, 20 indicates a rotor, 21 indicates a stator shell, 22 indicates a rotor shaft and 23 indicates a loading tank of the colloid mill 3.

EMBODIMENT OF THE INVENTION

Below is a more detailed description of the claimed invention that does not limit the scope of the claimed invention but demonstrates implementability of the invention by means of achieving the claimed technical result.

Figure 1:
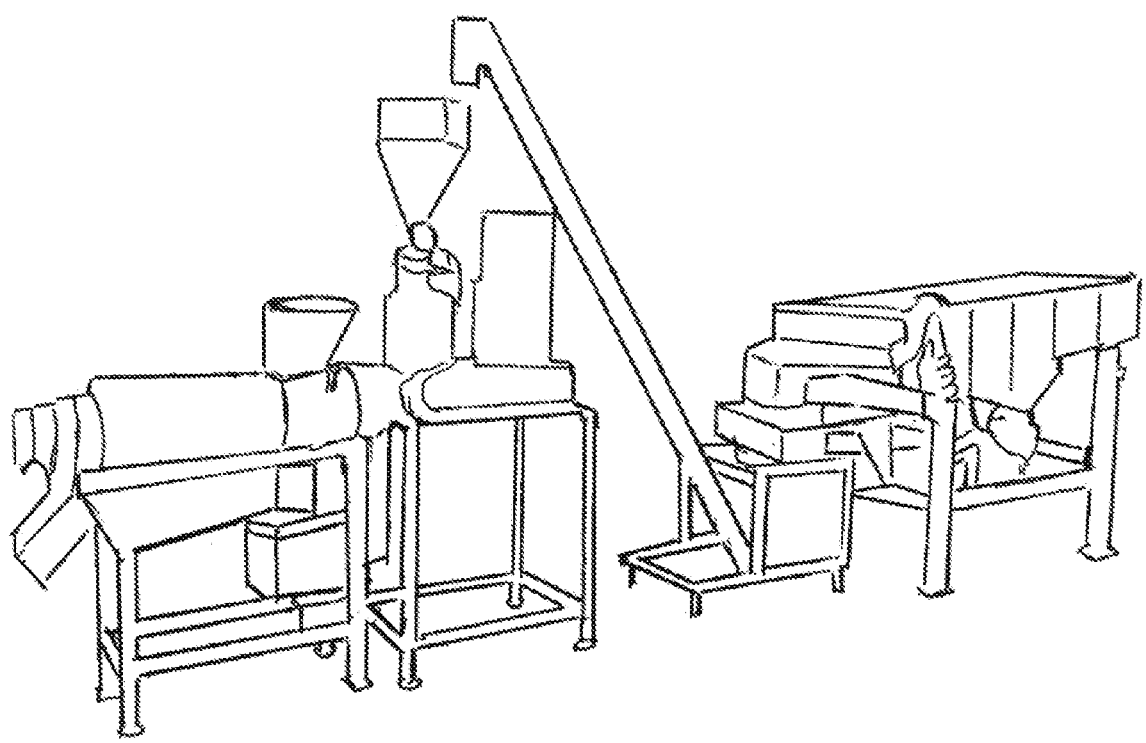
FIG. 1 demonstrates a picture of a part of the pilot production line consisting of a vibrating screen, a conveyor, a colloid mill and a screw extractor for obtaining protein suspension from brewer's grains.
Figure 2:
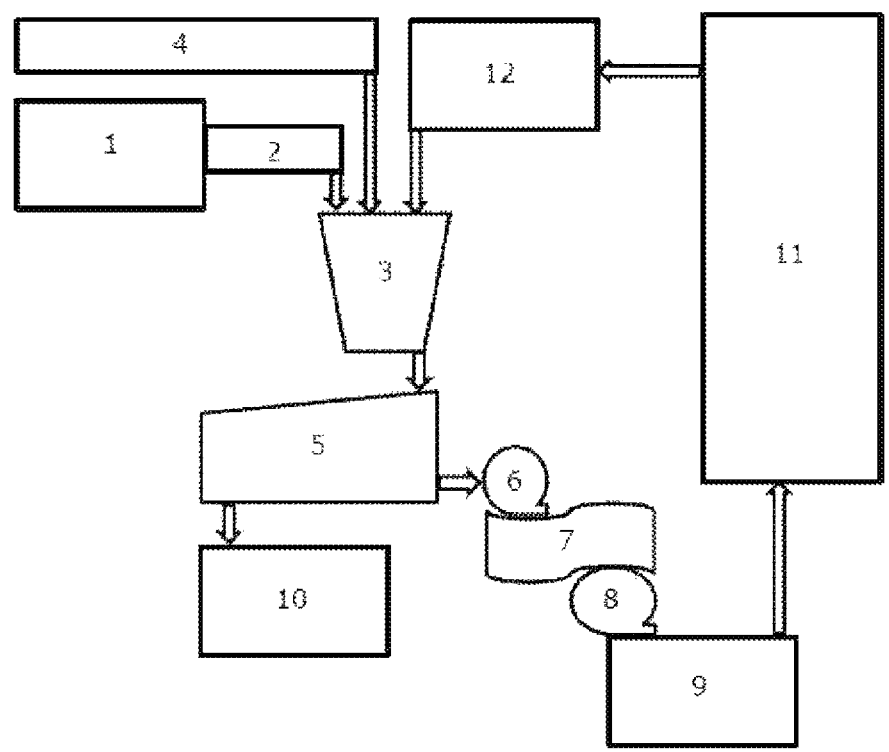
FIG. 2 demonstrates the production line's scheme for implementing the claimed method, where 1 indicates a vibrating screen, 2 indicates a conveyor, 3 indicates a colloid mill, 4 indicates a water pipeline, 5 indicates a screw extractor, 6 and 8 indicate impeller pumps, 7 indicates a vibration filter, 9 indicates a container for collecting protein suspension, 10 indicates a container for collecting husk, 11 indicates a block for processing the protein suspension in order to produce protein concentrate or protein isolate, 12 indicates a tank for centrate.

The source brewer's grains with the humidity level of 70-90% are subject to treatment in the course of 3 hours after they are produced (from the moment they are obtained as a waste product in the brewing industry). The temperature of such brewer's grains at the moment of their receipt form the production facility varies from 2° C. to 80° C. The brewer's grains are loaded manually or by means of any mechanical method on a vibrating screen 1 (FIGS. 1, 2) with the hole size of 6-10 mm equipped with a magnetic catcher where the brewer's grains are subject to loosening and removal of any mechanical and metallic foreign impurities. Treatment by means of this vibrating screen implies sieving of the brewer's grains with the vibration frequency from 10 to 50 Hz and the amplitude of 2-20 mm within 2-10 seconds in order to produce a raw material without lumps and of a homogeneous composition for the further processing stage when the material is subject to grinding. It is possible to obtain a homogeneous mass with removal of mechanical impurities in the course of loosening the brewer's grains not only by means of a vibrating screen but also by means of any prior art device or a set of devices performing the mentioned functions. For the purpose of grinding, the conveyor 2 takes the loosened brewer's grains to the colloid mill 3 (FIG. 3) or another grinding machine capable of producing 0.005-0.5 mm particles. At the same time, the raw material is loaded in the colloid mill's tank step-by-step and water is added in order to provide for homogeneous humidifying of the raw materials in volume that can be performed both in a continuous mode and in a pulsating mode. As a rule, the ratio of the supplied water to the brewer's grains in mass is from 0.5:1 to 1:1. The amount and rate of water supply can be calculated in advance based on the measured initial humidity parameters of the brewer's grains delivered for processing taking into account humidity losses in the course of sieving the brewer's grains by means of the vibrating screen. The humidity level of the brewer's grain subject to treatment in the colloid mill shall preferably be within the range of 90-95%. The colloid mill 3 performs its homogeneous mixing (and/or homogenization) in order to produce a homogeneous pasty mass (pulp) with the viscosity of preferably 750-1,400 cPa·s that moves by gravity to the screw extractor 5 where the mass is subject to additional grinding and division into suspension with the humidity level of 90-95% and the viscosity of 1.5 3 cPa·s and husk with the particle size from 0.01 mm to 1.0 mm and the humidity level of 60-75%. The temperature of the brewer's grains subject to treatment in the colloid mill and the screw extractor can vary from 2° C. to 90° C. The brewer's grains can be supplied to the colloid mill by means of any prior art technical device, for example by means of a screw conveyor, or a belt conveyor, or a drag conveyor.

Grinding of the brewer's grains in the colloid mill 3 takes place in the shell 21 between working surfaces of the rotor 20 and the stator 19, for example, in the course of rotation of the mill's rotor 20 at the rate of 1,800-3,200 rot./second what enables to produce thick, homogeneous, but sloppy consistency of the pulp for the maximum extraction of a nutritional fraction from the source raw material at the screw extraction stage. It is preferable to use centrate produced in the course of the food suspension's further treatment (in case of its concentrating) for its supply to the colloid mill 3 instead of water what provides for better extraction of the nutritional fraction remaining in the centrate and provides for avoiding a necessity of the centrate disposal, thus, for saving of resources necessary in case of the centrate disposal for purification before its discharge to the sewerage system. Water or centrate from blocks 5 or 12 is supplied to the V-shaped tank (receiving bunker) 23 of the colloid mill 3 via openings 14 of the water pipeline 13 located around the circumference of the tank in its upper part above the mark indicating the maximum tank load with raw materials. Amount of the supplied water or centrate can be regulated by means of the valve 18.

The openings 14 in the pipeline are preferably uniformly spaced along its length what ensures the total homogeneous humidifying (thinning) of the brewer's grains in the course of processing.

After grinding in the colloid mill 3 the pulp is subject to treatment in the screw extractor 5 with the screw rotation rate from 2 rot./minute to 8 rot./minute what enables to separate the food suspension from its waste product, barley's husk, in as short a time as possible, within 1-2 seconds. For this purpose, the pasty mass (pulp) produced by the colloid mill 3 fell by gravity into the screw extractor 5 where it was separated from the husk in order to produce the main product, the food suspension with the humidity level of max. 95%, and a waste product, barley's husk, with the humidity level of 60-75% and 1.0-5.0 mm husk particles. Since after treatment in the screw extractor 5 the suspension still contains 2-5% of small husk particles from 0.01 to 1.0 mm, this suspension is delivered by means of the impeller or another pump 6 designed for work with food suspension with the impurity level of up to 5% represented by small vegetable fractions of max. 1.0 mm, for the next purification stage to the vibration filter 7 with the filter holes of 0.2-0.5 mm what practically provides for removal from the food suspension of husk remaining after the screw extraction stage. After the vibration filter 7 the suspension is pumped to the collection tank 9 by means of the impeller pump 8. The produced protein suspension with the protein content of 50-65% wt (dry solid) can be the final product that can be used as a food or feed supplement and it can also be frozen for its further use. The produced protein suspension can be sent for its further processing treatment to the block 11 for the purpose of producing protein concentrate with the protein content of 60-80% wt or protein isolate with the protein content of min. 80% wt.

Husk is a waste product of the brewer's grains processing and in the course of the screw extractor's operation husk naturally falls in the collection bunker from which it is delivered to the collection tank by means of a screw conveyor, or a spiral conveyor or any other conveyor. The claimed machine can be used for producing protein suspension with the protein content of max. 50% wt, for example 40, 42, 47 and 49% wt (with a lower energy value) in case of respective settings of devices enabling to produce suspension particles of the upper level of the claimed size range (more than 0.5 mm). Such product can be used in fields where there are no requirements to achieving the greatest possible quantitative content of protein in a protein product, for example, when it is used as animal food stuff.

Food protein suspension in the amount of 337 litres was produced by means of the claimed method with its further drying for analysis.

For this purpose 260 kg of brewer's grains with the humidity level of 75.59% (original composition, energy value of 150 kcal) were manually loaded on the vibrating screen 1 represented by the vibrating table unit XFZ1020 with a single-level screen and 10 mm holes, with the table unit length of 2,000 mm, with the table unit width of 1,000 mm, with the vibration frequency of 20 Hz and the vibration amplitude of 8 mm. From the vibrating screen 1 the mass by means of the belt conveyor 2 was supplied to the colloid mill 3 represented by the unit KDDJ-1,5 with the power capacity of 11 kW, with the rotation rate of 2,200 rot./minute of the rotor 20 that can also be equipped with a device for supplying drinking water from the block 4. In the colloid mill, the brewer's grains were humidified by means of water with the design amount of 170 litres (0.67:1) that was supplied to the colloid mill at the rate of 15 litres per minute. At the same time, the humidified brewer's grains were subject to grinding in order to obtain the faction of 0.1-0.9 mm. The process of supplying the source raw materials and water to the loading tank 23 of the colloid mill 3 was controlled by means of three level-sensing devices 15, 16 and 17 built in the shell of the loading tank 23 and a microcontroller located close to the level-sensing devices at the frame of the table on which the colloid mill was installed. At the same time one of the level-sensing device, the upper one, 17 was used for controlling the maximum possible load of the raw material in the bunker (85-90% in volume of the maximum capacity of the bunker); when this level was reached a command to stop the loading conveyor was given; the second level-sensing device, the middle one, 16 was used for controlling the minimum level of the loaded raw material (25-30% in volume of the maximum capacity of the bunker); when this level was reached a command to start the loading conveyor and to supply the raw material was given what provided for continuous operation of the colloid mill. The third level-sensing device, the lower one, 15 was installed near the loading bunker's bottom at the distance of 15 cm from the bottom and it was used for controlling the minimum possible load of the raw material in the bunker (10-15% in volume of the maximum capacity of the bunker); if this level was not reached the colloid mill stopped until another portion of the raw material was supplied. After the colloid mill, the produced pulp with the viscosity of 900-1, 200 cPa and the humidity level of 95% was delivered to the screw extractor 5 represented by the machine of KDLZ-1,5 model with the power capacity of 4 kW, with the rotation rate of 4.5-10 rot./minute. The output was the main product, food suspension with the humidity level of 95% and the viscosity of 2.013 cPa, and a waste product, barley's husk, with the humidity level of 70.84%. By means of the impeller pump 6 with the power capacity of 0.25 kW with the rotation rate of 1,200 rot./minute the food suspension was delivered to the vibration filter 7 of XZS-1200-1S model with the power capacity of 0.75 kW with 0.3 mm openings. After filtration by means of the impeller pump 8 with the power capacity of 0.25 kW with the rotation rate of 1,200 rot./ minute the food suspension was pumped to the collection tank 9. The husk naturally fell in the collection tank 10. Thus, the food suspension with the humidity level of 93%, with the viscosity of 1.907 cPa and the particle size of 0.005-0.3 mm was produced. In order to assess its composition, 12 litres of suspension were dried in the spray-type drier HT-RY1500 during 8 hours at the temperature of 200° C. until the humidity reached the level of 10% (capacity of this spray-type drier HT-RY1500 amounts to 1,500 ml of suspension per hour). The analysis showed that the obtained food suspension (sample 1) is characterized by nutritional energy value of 250 kcal and the following composition, % wt (dry solid) (Table 1):

TABLE 1

| Composition | Brewer's grains (original composition), % wt | Food suspension, % wt (sample 1) |
|---|---|---|
| Protein | 18.98 | 51.16 |
| Fats | 7.9 | 4.9 |
| Fibre | 13.6 | 4.5 |
| Ash | 2.2 | 0.8 |
| at the same time protein from brewer's gains is rich in the following amino acids: | | |
| Arginine | 1.07 | 4.27 |
| Lysine | 0.86 | 2.37 |
| Tyrosine | 0.61 | 2.55 |
| Phenylalanine | 1.23 | 3.57 |
| Histidine | 0.66 | 1.8 |
| Isoleucine | 0.79 | 3.79 |
| Leucine | 0.57 | |
| Methionine | 0.5 | 1.5 |
| Valine | 1.06 | 2.62 |
| Proline | 2.05 | 4.21 |
| Threonine | 0.77 | 2.26 |
| Serine | 0.89 | 1.79 |
| Alanine | 0.94 | 3.6 |
| Glycine | 0.79 | 2.19 |
| Cystine | 0.46 | 1.91 |
| Glutamic acid | 4.57 | 8.63 |
| Asparaginic acid | 1.35 | 2.06 |
| Total amount of amino acids | 19.17 | 49.12 |

The total time for processing 260 kg of brewer's grains amounted to 25 minutes.

Thus, the protein suspension produced by means of the claimed method is characterized by a high protein content with preservation of the amino acid composition of the brewer's grains and a low content of fats and fibres. The method is easy to implement and does not take a lot of time: the time from loading raw material in the machine to obtaining the final product in the form of suspension, for example when calculated for 100 kg of brewer's grains, takes from 5 to 10 minutes with the equipment's capacity from 20 to 500 tonnes/day; at the same time, the amount of centrate being a waste product and subject to disposal is minimal and it is equal to max. 1% of the capacity of the brewer's grain processing line of kg/1 minute.

Brewer's grains delivered from five different manufacturing facilities were processed by this machine in accordance with the claimed method. The quantitative content of ingredients in the brewer's grains compositions was different from the original composition specified in table 1 within the limit of 1-5%. Table 2 shows compositions of protein suspensions with the optimal content of key components.

TABLE 2

| Parameters | Food suspension | | | | |
|---|---|---|---|---|---|
| | sample 2 | sample 3 | sample 4 | sample 5 | sample 6 |
| nutritional energy value (dry solid) | 245 kcal | 260 kcal | 258 kcal | 255 kcal | 265 kcal |
| humidity | 91% | 93% | 92% | 93% | 95% |
| particle size | 0.005-0.5 mm | 0.005-0.1 mm | 0.005-0.3 | 0.005-0.4 mm | 0.005-0.1 mm |
| Composition | content (% wt) | | | | |
| Protein | 51.1 | 62.19 | 58.3 | 55.4 | 64.7 |
| Fats | 3.7 | 4.9 | 3.2 | 3.8 | 4.7 |
| Fibre | 2.4 | 3.8 | 4.2 | 3.1 | 4.5 |
| Ash | 0.4 | 0.82 | 0.56 | 0.7 | 1.0 |
| Amino acid composition: | | | | | |
| Arginine | 3.93 | 4.27 | 4.6 | 4.0 | 5.3 |
| Lysine | 1.95 | 3 | 2.72 | 2.87 | 3.17 |
| Tyrosine | 2.15 | 3.85 | 2.53 | 2.23 | 3.72 |
| Phenylalanine | 3.5 | 4.97 | 4.47 | 3.68 | 4.17 |
| Histidine | 2.1 | 2.9 | 2.1 | 1.85 | 2.1 |
| Isoleucine/Leucine | 2.23 | 3.79 | 2.05 | 2.89 | 3.82 |
| Methionine | 2.43 | 2.55 | 2.1 | 1.97 | 2.1 |
| Valine | 2.84 | 2.62 | 2.9 | 2.75 | 3.16 |
| Proline | 3.85 | 4.73 | 4.1 | 3.95 | 5.1 |
| Threonine | 1.79 | 3.12 | 3.7 | 3.17 | 3.7 |
| Serine | 1.98 | 2.3 | 2.4 | 1.95 | 2.4 |
| Alanine | 2.84 | 4.1 | 4.3 | 3.97 | 4.3 |
| Glycine | 2.98 | 2.49 | 3.1 | 2.94 | 3.1 |
| Cystine | 2.62 | 2.1 | 2.4 | 1.95 | 2.4 |
| Glutamic acid | 7.7 | 9.8 | 8.5 | 7.94 | 10.3 |
| Asparaginic acid | 2.35 | 3.2 | 2.6 | 2.27 | 3.4 |
| Total amount of amino acids | 47.24 | 59.79 | 54.57 | 50.38 | 62.24 |

Table 3 include parameters of processing brewer's grains (samples 2-6).

TABLE 3

| Equipment | Processing parameters | | | | |
|---|---|---|---|---|---|
| | sample 2 | sample 3 | sample 4 | sample 5 | sample 6 |
| Colloid mill/rotor rotation rate (rot./second) | 1.800 | 3,000 | 2,500 | 2.000 | 3,200 |
| Vibrating screen screen hole size (mm)/vibration frequency (Hz and mm) | 10/10, 15 | 5/40, 10 | 7/30, 20 | 8/20, 15 | 6/50, 8 |
| Screw extractor/rotation rate (rot./second) | 3 | 8 | 5 | 7 | 10 |
| Filtration/hole size (mm) | 0.5 | 0.1 | 0.3 | 0.4 | 0.1 |

Based on the above-given data it can be concluded that a protein product in the form of suspension with a high protein content is produced despite the fact that various plants use different types of barley, have various technologies for manufacturing brewer's malt, various malt mix recipes for manufacturing beer etc. The two-stage processing of brewer's grains (in the colloid mill and in the screw extractor) without using multi-step compression processes and thermochemical treatment enables to obtain a protein product with the humidity level of max. 95% and the particle size of max. 0.5 mm with the protein content of min. 50.0% wt (dry solid) and without gluten.

This method of producing protein suspension is universal and enables to preserve all valuable biologically active agents of the source brewer's grains. The rich chemical composition of brewer's grains with the minimal content of hydrocarbons predetermines its prospects in the food-processing industry, in particular its use as an albuminous vitamin-mineral additive in manufacturing of pastry products.

The invention claimed is:

1. A method for producing a protein suspension having a moisture content equal to or less than 95%; a particle size of equal to or less than 0.5 mm and comprising fat, fiber, ash and protein; wherein the total protein content is of at least 55% dry wt, the method comprising:
   i) loosening brewer's grains to obtain a homogeneous mass,
   ii) removing impurities from the homogenous mass;
   iii) grinding the homogenous mass obtained in ii) with a colloid mill while hydrating the homogenous mass with water or centrate to reach a moisture content of between 90 and 95% and particle size of between 0.1 mm and 0.9 mm to obtain a pasty mass, wherein:
      the hydrating the homogeneous mass with the water or centrate is for homogeneous humidification of the pasty mass in a volume; and
      the pasty mass has a viscosity of between 750 cPa·s and 1400 cPa·s that moves by gravity to a screw extractor where the pasty mass is subject to additional grinding and separation to produce the protein suspension with a viscosity of between 1.5 and 3 cPa·s.

2. The method of claim 1, wherein step iii) is performed at a rotor rate of 1,800-3,200 rot./second.

3. The method of claim 1, wherein the additional grinding and separation comprises removing, by the screw extractor, a ground husk from the pasty mass.

4. The method of claim 1, wherein the water or centrate is supplied to a receiving bunker of the colloid mill via openings of the water pipeline located around the circumference of the receiving bunker in its upper part.

5. The method of claim 1, wherein the brewer's grains are loosened, and impurities are removed by means of a vibrating screen with hole size of between 6 and 10 mm, and a screen vibration frequency of between 10 and 50 Hz and an amplitude of between 2 and 20 mm.

6. The method of claim 1, wherein the protein suspension is subject to additional vibrating filtration.

7. The method of claim 6, wherein the additional vibrating filtration is performed with screens having a hole size of between 0.1 and 0.5 mm.

8. The method of claim 4, wherein openings in the water pipeline are uniformly spaced along its length in order to ensure the homogeneous humidification of the pasty mass.

* * * * *